US006838586B2

(12) United States Patent
Mertens et al.

(10) Patent No.: US 6,838,586 B2
(45) Date of Patent: Jan. 4, 2005

(54) PROCESS FOR THE SYNTHESIS OF SILICOALUMINOPHOSPHATE MOLECULAR SIEVES

(75) Inventors: Machteld M. Mertens, Boortmeerbeek (BE); Brita Engels, Betekom (BE); Ronald G. Searle, Houston, TX (US); Grigore Pop, Bucharest (RO); Irina Rodica Tamas, Bucharest (RO); Rodica Ganea, Bucharest (RO); Ruxandra Birjega, Bucharest (RO)

(73) Assignee: Exxon Mobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/335,613

(22) Filed: Dec. 31, 2002

(65) Prior Publication Data

US 2003/0092951 A1 May 15, 2003

Related U.S. Application Data

(62) Division of application No. 09/677,492, filed on Oct. 2, 2000, now Pat. No. 6,514,899.

(30) Foreign Application Priority Data

Oct. 1, 1999 (WO) .............................. PCT/RO99/00015

(51) Int. Cl.$^7$ ................................................ C07C 1/02
(52) U.S. Cl. .......................... 585/640; 585/638; 585/639
(58) Field of Search .................................. 585/638, 639, 585/640

(56) References Cited

U.S. PATENT DOCUMENTS

| 4,499,327 | A | * | 2/1985 | Kaiser | ........................ 585/640 |
| 4,752,651 | A | * | 6/1988 | Kaiser | ........................ 585/640 |
| 4,943,424 | A | * | 7/1990 | Miller | ........................ 423/708 |
| 5,962,762 | A | * | 10/1999 | Sun et al. | ................... 585/640 |
| 6,004,898 | A | * | 12/1999 | Sun | ............................ 502/214 |
| 6,040,264 | A | * | 3/2000 | Sun et al. | ................... 502/214 |
| 6,162,415 | A | * | 12/2000 | Liu et al. | .................... 423/706 |
| 6,514,899 | B1 | * | 2/2003 | Mertens et al. | ............. 502/214 |

* cited by examiner

Primary Examiner—Kiley Stoner
Assistant Examiner—Christina Ildebrando

(57) ABSTRACT

The invention is directed to a method for making a silicoaluminophosphate (SAPO) molecular sieve from a reaction mixture comprising components present in amounts sufficient to form the SAPO, the reaction mixture having a first pH. The method comprises the steps of: adding an acid to the reaction mixture after the reaction mixture undergoes a change in pH from the first pH; and crystallizing the SAPO from the reaction mixture. The present invention is also directed to a silicoaluminophosphate molecular sieve made by this process.

16 Claims, No Drawings

PROCESS FOR THE SYNTHESIS OF SILICOALUMINOPHOSPHATE MOLECULAR SIEVES

PRIORITY CLAIM

This Application is a Divisional of Ser. No. 09/677,492, filed Oct. 2, 2000, now U.S. Pat. No. 6,514,899 which claims priority to PCT Application No. PCT/RO99/00015, filed Oct. 1, 1999 and entitled, "Process for the Synthesis of Silicoaluminophosphate Molecular Sieves."

FIELD OF THE INVENTION

The present invention relates to a process for the synthesis of silicoaluminophosphate molecular sieves.

BACKGROUND OF THE INVENTION

Light olefins, defined herein as ethylene, propylene, and mixtures thereof, serve as feeds for the production of numerous important chemicals and polymers. Light olefins traditionally are produced by cracking petroleum feeds. Because of a limited supply of competitive petroleum feeds, the opportunities to produce low cost light olefins from petroleum feeds are limited. Efforts to develop light olefin production technologies, based on alternative feeds, have increased.

An important type of alternate feed for the production of light olefins are oxygenates, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates show promise as economical, non-petroleum sources for light olefin production.

Typically, oxygenates are converted to an olefin product through a catalytic process. The conversion of a feed containing oxygenates is usually conducted in the presence of a molecular sieve catalyst. Although ZSM-type molecular sieves and other molecular sieves may be used for the production of olefins from oxygenates, research has found silicoaluminophosphate (SAPO) molecular sieves to be of particular value in the catalytic process.

While SAPO molecular sieves are thought to be the most useful, synthesis of this type of catalyst is expensive because of the low yield of molecular sieve provided by the reaction mixture used to formulate this type of molecular sieve. In a SAPO synthesis procedure, a silica source, an alumina source, a phosphorous source and a templating agent are combined to form a reaction mixture. The SAPO molecular sieve is then crystallized over a period of time, typically a period of several hours to is several days, from the reaction mixture.

The synthesis of SAPOs is sensitive to small variations in the reaction mixture composition and reaction mixture preparation. These sensitivities vary from one type of SAPO to another. One critical parameter of the synthesis procedure is the pH of the reaction mixture. At the start of a SAPO synthesis, the reaction mixture, sometimes referred to in the art as the "final" reaction mixture, has an initial pH. As the synthesis proceeds, the pH of the reaction mixture increases. It has been found that this increase in pH makes it difficult for the SAPO molecular sieve to crystallize from the reaction mixture even in the presence of excess quantities of the silica source, the alumina source, the phosphorous source and the template, and this pH increase eventually causes the synthesis reaction to cease.

Romanian Patent No. 114,524 B1 describes a process for forming a SAPO molecular sieve, particularly for forming SAPO-34. In the process disclosed in the '524 patent, a solution of tetraethylammonium phosphate with a concentration of 25% is prepared using a conventional method from triethylamine, ethyl bromide and 73% concentrated phosphoric acid. Hydrated alumina with an $Al_2O_3$ content of 65%, of which 40% is bayerite, is suspended in demineralized water and introduced, under agitation, into a zeolitization autoclave after the solution of tetraethylammonium phosphate was introduced to the autoclave. Under continuous agitation, a silica sol which is stabilized with ammonia and which has a content of 28% $SiO_2$ is introduced to the autoclave. The pH of the resultant suspension is then adjusted to 6.3–6.5 with phosphoric acid.

The zeolitization process is conducted in six successive steps. In the first step, 15% of the entire charge is introduced into an autoclave. The temperature is then increased to 198–205° C. and maintained at that point for 20 hours. The autoclave is cooled to 30–40° C. and an additional quantity of the suspension is introduced to the autoclave. After addition of an additional amount of the suspension, the process is resumed at 198–205° C. The operation is repeated for an additional period of five hours. The entire zeolitization process lasts for 100 hours. This time period includes the steps of cooling and heating which last for 2–3 hours each.

WO 99/19254 describes a method for making molecular sieves comprising SAPO-44. In a preferable version of the process for making SAPO-44, the pH of the final reaction mixture (containing a silicon component, a phosphorous component, an aluminum component and a template) is maintained in the range from about 5.5 to about 8.5, preferably from about 6 to about 8. This reference teaches that the pH value of the final reaction mixture may be adjusted, if desired, by either adding an appropriate amount of a base, such as ammonia/ammonia hydroxide, to increase the pH, or an appropriate amount of a suitable inorganic or organic acid, such as phosphoric acid, HCl, acetic acid, formic acid, $CO_2$ and others, to decrease the pH.

With the aforementioned methods and other methods currently in use the art, an initial pH adjustment to the reaction mixture helps to establish appropriate conditions for the formation of a SAPO molecular sieve. These methods, however, do not alleviate or prevent the pH increase which occurs as the synthesis reaction continues. As discussed above, this pH increase drives the synthesis reaction to completion even in the presence of excess building materials for the sieve, often providing low yields of the molecular sieve. Thus, a need exists in the art for improved methods for synthesizing SAPO molecular sieves.

SUMMARY OF THE INVENTION

In order to overcome many of the problems inherent in the prior art, the present invention provides a method for the synthesis of silicoaluminophosphate (SAPO) molecular sieves.

As used herein, the term "initial pH" or "first pH" refers to the pH of the reaction mixture immediately after it has been formed from the phosphorous-containing composition, the aluminum-containing composition, the silicon-containing composition and the template, prior to any heating of the reaction mixture and after any pH adjustments to the reaction mixture, such as disclosed in the art.

One aspect of the present invention is directed to a method for forming a silicoaluminophosphate (SAPO) molecular sieve. The method comprises the following steps: providing a source of a silicon-containing composition; providing a source of an aluminum-containing composition; providing a source of a phosphorous-containing composition; providing a template; forming a reaction mixture sufficient to form a SAPO molecular sieve from the source of a silicon-containing composition, the source of an aluminum-containing composition, the source of a phosphorous-containing composition, and the template, the reaction mixture having a first pH; determining a pH increase in the reaction mixture such that the reaction mixture has a second pH higher than the first pH; and adding, after the determining the pH increase, an acid to the reaction mixture to adjust the second pH to from the first pH plus about one pH unit to the first pH minus about one pH unit. The present invention is also directed to a silicoaluminophosphate molecular sieve made by this process.

This aspect of the invention may also include the following steps: dissolving at least a portion of the crystals of the SAPO molecular sieve in the reaction mixture; adding an acid to the reaction mixture; and re-crystallizing crystals of the SAPO molecular sieve from the reaction mixture.

Another aspect of the present invention is directed to a method for making a silicoaluminophosphate (SAPO) molecular sieve from a reaction mixture comprising components present in amounts sufficient to form the SAPO, the reaction mixture having a first pH. The method comprises the steps of: adding an acid to the reaction mixture after the reaction mixture undergoes a change in pH from the first pH; and crystallizing the SAPO from the reaction mixture. The present invention is also directed to a silicoaluminophosphate molecular sieve made by this process.

Yet another aspect of the present invention is directed to a method for forming a silicoaluminophosphate 34 (SAPO-34) molecular sieve. This method comprises the following steps: providing a source of a silicon-containing composition; providing a source of an aluminum-containing composition; providing a source of a phosphorous-containing composition; providing a template; forming a reaction mixture sufficient to form SAPO-34 from the source of a silicon-containing composition, the source of an aluminum-containing composition, the source of a phosphorous-containing composition, and the template, the reaction mixture having a first pH of from about 5.5 to about 8.5; determining a change in pH of the reaction mixture such that the reaction mixture has a second pH higher than the first pH; and adding, after determining the change in pH, an acid to the reaction mixture to adjust the second pH of the reaction mixture to a pH of from about 5.5 to about 8.5. The present invention is also directed a SAPO-34 molecular sieve made by this process.

Still another aspect of the present invention is directed to a method for converting an oxygenate to an olefin. The method comprises contacting an oxygenate with a silicoaluminophosphate (SAPO) molecular sieve catalyst under conditions effective to convert the oxygenate to an olefin. In this process, the SAPO molecular sieve is made by the process comprising the following steps: providing a source of a silicon-containing composition; providing a source of an aluminum-containing composition; providing a source of a phosphorous-containing composition; providing a template; forming a reaction mixture sufficient to form a SAPO molecular sieve from the source of a silicon-containing composition, the source of an aluminum-containing composition, the source of a phosphorous-containing composition, and the template, the reaction mixture having a first pH; determining a pH increase in the reaction mixture such that the reaction mixture has a second pH higher than the first pH; and adding, after the determining the pH increase, an acid to the reaction mixture to adjust the second pH to from the first pH plus about one pH unit to the first pH minus about one pH unit.

Other advantages and uses of the present invention will become apparent from the following detailed description and appended claims.

DETAILED DESCRIPTION OF THE INVENTION

In the present invention, the applicants have discovered that the addition of an acid source to a SAPO reaction mixture, during the crystallization of a SAPO molecular sieve from the reaction mixture, produces improved yields of SAPO molecular sieves from the reaction mixture.

The process of the present invention may be used to form silicoaluminophosphate molecular sieves selected from the group including SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and the metal substituted forms thereof. Preferably, the method of the present invention is used to form SAPOs selected from the group including SAPO-5, SAPO-11, SAPO-20, SAPO-31, SAPO-34, and SAPO-24. Most particularly, the process of the present invention is used to produce SAPO-34.

Silicoaluminophosphate molecular sieves are generally classified as microporous materials having 8, 10, or 12 membered ring structures. These ring structures can have an average pore size ranging from about 3.5–15 angstroms. When used to convert oxygenates to olefins, the preferred SAPO is a small pore SAPO molecular sieve having an average pore size ranging from about 3.5 to 5 angstroms, more preferably from 4.0 to 5.0 angstroms. These preferred pore sizes are typical of molecular sieves having 8 membered rings.

The SAPO molecular sieves formed by the method of this invention comprise a three-dimensional microporous crystal framework structure of $[SiO_2]$, $[AlO_2]$ and $[PO_2]$ corner-sharing tetrahedral units. This type of framework is effective in converting various oxygenates into olefin products.

The $[PO_2]$ tetrahedral units within the framework structure of the molecular sieve produced by this invention can be provided by a variety of compositions. Examples of these phosphorus-containing compositions include phosphoric acid, organic phosphates such as triethyl phosphate, tetraethyl-ammonium phosphate, and aluminophosphates. The phosphorous-containing compositions are mixed with reactive silicon and aluminum-containing compositions under the appropriate conditions to from the molecular sieve.

The $[AlO_2]$ tetrahedral units within the framework structure can be provided by a variety of compositions. Examples of these aluminum-containing compositions include aluminumalkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to from the molecular sieve.

The [SiO$_2$] tetrahedral units within the framework structure can be provided by a variety of compositions. Examples of these silicon-containing compositions include silica sols, colloidal silicas, such as Cab-O-Sil®, pyrogenic silicas, and silicium alkoxides, such as tetra ethyl orthosilicate. High surface area silicas such as Aerosil®-type silicas may also be used. The silicon-containing compositions are mixed with reactive aluminum and phosphorus-containing compositions under the appropriate conditions to form the molecular sieve.

Substituted SAPOs can also be formed in this invention. These compounds are generally known as MeAPSOs or metal-containing silicoaluminophosphates. The metal can be selected from the group consisting of an alkali metal ion (Group IA), an alkaline earth metal ion (Group IIA), a rare earth ion (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and a transition cation from one of Groups IVB, VB, VIB, VIIB, VIIIB, and IB.

Preferably, the Me represents an atom such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is −2, −1, 0, +1, and +2, respectively. Incorporation of the metal component is typically accomplished adding the metal component during synthesis of the molecular. However, post-synthesis ion exchange can also be used. See, for example, U.S. Ser. No. 08/571,506, in which the description of the post-synthesis ion exchange method is described. This application is fully incorporated herein by reference.

The reaction mixture also contains one or more templates. Templates are structure directing agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another sieve. When two templates are used, the template is referred to as a dual template.

Representative templates include tetraethyl ammonium hydroxide (TEAOH), tetraethylammonium phosphate (TEAP), cyclopentylamine, aminomethyl cyclohexane, piperidine, triethylamine, cyclohexylamine, tri-ethyl hydroxyethylamine, morpholine, dipropylamine (DPA), pyridine, isopropylamine (IPA) and combinations thereof. Preferred templates are triethylamine, cyclohexylamine, piperidine, pyridine, isopropylamine, TEAOH, DPA, TEAP and mixtures thereof. TEAP may serve as both a source of a phosphorus-containing composition and as a template. When TEAP is used, the phosphorus-containing composition and the template are the same material. The present invention may employ a "dual template." For the purposes of the present invention, a "dual template" is a combination of two templates selected from the previous list of useful templates. A desired dual template for the formation of SAPO-34 comprises TEAOH and DPA or IPA.

SAPO molecular sieves are synthesized by hydrothermal crystallization methods generally known in the art. See, for example, U.S. Pat. Nos. 4,440,871; 4,861,743; 5,096,684; and 5,126,308; all of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100-250° C., until a crystalline product is formed. In the present invention, the reaction mixture may be heated by conventional heating methods such as electrical, steam or oil heaters, or by microwave energy from a microwave source. Formation of the crystalline product can take anywhere from around 2 hours to as long as 2 weeks. In some cases, stirring or seeding with crystalline material will facilitate the formation of the product.

The sieve can be recovered from the reaction mixture by standard means, such as by centrifugation or filtration. The product can also be washed, recovered by the same means and dried.

The applicants have discovered that, when the pH of the reaction mixture is adjusted by the addition of an acid to the reaction mixture, the crystallization process is accelerated and, in the case of some molecular sieves, the yields of the molecular sieve can be increased. In the process of the present invention, the pH of the reaction mixture is adjusted after the reaction mixture undergoes a change in pH from an initial or first pH. Typically, although not necessarily, this pH change occurs after the reaction mixture has been heated. The change in pH indicates that the molecular sieve is beginning the crystallization process from the reaction mixture or has begun to crystallize from the reaction mixture. Desirably, the acid is added to the reaction mixture during heating of the reaction mixture.

The pH of the reaction mixture is adjusted to approximately the pH of the original reaction mixture plus or minus one pH unit. Desirably, the pH of the reaction mixture is adjusted to approximately the initial pH of the reaction mixture plus or minus 0.5 pH unit. More desirably, the pH of the reaction mixture is adjusted to approximately the initial pH of the reaction mixture. For the purposes of this invention, "approximately the initial pH" means the initial pH plus or minus 0.2 pH unit. Most desirably, the pH of the reaction mixture is adjusted back to the original pH of the reaction mixture.

In order to adjust the pH of the reaction mixture, it may be necessary to interrupt the crystallization process so the pH of the reaction mixture can be measured to determine how much acid should be added to the reaction mixture to adjust the pH. Typically, because a reaction mixture is heated to facilitate the crystallization process, the reaction mixture must be cooled prior to either a pH measurement or the addition of the acid. However, it is not necessary to interrupt the crystallization process as the pH of the reaction mixture can be monitored by a pH measuring device. It is also possible to add acid to the reaction mixture without measuring the pH of the reaction mixture if appropriate time for addition of the acid has been determined from prior experimentation or experience. The acid may or may not be heated prior to addition to the reaction mixture.

The pH of the reaction mixture is adjusted on either a discontinuous basis or continuous basis. By "discontinuous," it is meant the addition of the acid to the reaction mixture occurs for a discrete period of time. The discontinuous addition of the acid to the reaction mixture occurs at least one time and may occur as many times as necessary to provide the reaction mixture with the target pH. By "continuous," it is meant that the addition of the acid to the reaction mixture takes place uninterrupted in time. The continuous addition of the acid to the reaction mixture is particularly useful in large-scale syntheses. In such a process, the pH of the reaction mixture is measured by a continuous feed loop of reaction mixture to a pH measuring device. The pH measuring device then controls the addition of the acid to the reaction mixture. The continuous addition of acid to the reaction mixture also serves to moderate any pH fluctuations which may occur in the reaction mixture.

Organic and inorganic acids are both useful for adjusting the pH of the reaction mixture to approximately the initial pH of the reaction mixture. These acids are selected from group consisting of phosphoric acid, hydrochloric acid, sulfuric acid, nitric acid, carbonic acid, acetic acid and formic acid. Desirably, phosphoric acid is used because this acid can also serve as a phosphorous source for the formation of the SAPO. It has also been discovered that if the phosphorous containing compound used to form the sieve is a phosphoric acid, it is desirable that the acid added to the reaction mixture to adjust the pH of the reaction mixture be a phosphoric acid.

As an optional step in this process, any molecular sieve crystals which have formed from the reaction mixture may be separated from the reaction mixture prior to addition of the acid to the reaction mixture. In a continuous molecular sieve forming process, the molecular sieve crystals may be continuously separated from the reaction mixture. It is particularly easy to separate the crystals from the reaction mixture if the reaction mixture is cooled prior to the addition of the acid. Useful separation methods include, for example, centrifugation and filtration.

As stated above, the process of the present invention is desirably used to formulate SAPO-34 molecular sieves. When SAPO-34 is formed by the process of the present invention, the reaction mixture has a pH of from about 5.5 to about 8.5. During the crystallization process, the pH is adjusted to be from about 5.5 to about 8.5 and, desirably, from 6 to 8. More desirably, the pH is adjusted to from about 6.2 to about 7.8.

In another embodiment of the present invention, the applicants have discovered that SAPO crystals can be re-crystallized from the reaction mixture after having at least partially dissolved in the reaction mixture. For example, once a crystallization reaction has been completed, the reaction mixture, which contains the crystals formed in the crystallization reaction, may remain unattended and, as a result, at least a portion of the crystals return to solution in the reaction mixture. In order to cause the dissolved materials to recrystallize from the reaction mixture, acid is added to the reaction mixture to adjust the pH of the reaction mixture to a pH substantially equal to the initial pH of the reaction mixture. Prior to adding the acid, any crystals in the reaction mixture may separated from the reaction mixture by the method described above. Desirably, the crystals are recovered from the reaction mixture at or above room temperature.

The pH adjustment causes the crystals to re-crystallize from the reaction mixture. Desirably, the pH of the reaction mixture is adjusted to approximately the pH of the original reaction mixture plus or minus one pH unit. More desirably, the pH of the reaction mixture is adjusted to approximately the pH of the original reaction mixture plus or minus 0.5 pH unit. Most desirably, the pH of the reaction mixture is adjusted to the initial pH plus or minus 0.2 pH unit. The crystals are then recovered from the reaction mixture as described above.

As a result of the crystallization process of SAPO molecular sieves, the recovered sieve typically contains within its pores at least a portion of the template used in making the initial reaction mixture. The crystalline structure essentially surrounds the template, and the template must be removed to obtain catalytic activity. Once the template is removed, the crystalline structure that remains has what is typically referred to as an intracrystalline pore system.

In many cases, depending upon the nature of the final product formed, the template may be too large to move freely through the intracrystalline pore system. In such a case, the template is removed by a heat treatment process. For example, the template can be calcined, or essentially combusted, in the presence of an oxygen-containing gas, by contacting the template-containing sieve in the presence of the oxygen-containing gas and heating at temperatures from 200° C. to 800° C. Thus, the processes of the present invention may also include the optional step of removing the template from the molecular sieve.

The silicoaluminophosphate molecular sieves may be admixed (blended) with other materials. When blended, the resulting composition is typically referred to as a silicoaluminophosphate (SAPO) catalyst, with the catalyst comprising the SAPO molecular sieve.

Materials which can be blended with the molecular sieve are various inert or binder materials. These materials include compositions such as kaolin and other clays, various forms of alumina or alumina sol, titania, zirconia, quartz, silica or silica or silica sol, and mixtures thereof. These components are also effective in reducing overall catalyst cost, acting as a thermal sink to assist in heat shielding the catalyst during regeneration, densifying the catalyst and increasing catalyst strength. When blended with inert or binder materials, the amount of molecular sieve which is contained in the final catalyst product ranges from 10 to 90 weight percent, preferably 30 to 70 weight percent. The invention can still be accomplished while the molecular sieve is included in a blend of inert and/or binder materials.

In still another embodiment of this invention, a feed containing an oxygenate is contacted in a reaction zone of a reactor apparatus with a SAPO, produced by the method described above, at process conditions effective to produce light olefins, i.e., an effective temperature, pressure, WHSV (weight hour space velocity) and, optionally, an effective amount of diluent, correlated to produce light olefins. These conditions are described in detail below. Usually, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor includes not only commercial scale reactors but also pilot sized reactor units and lab bench scale reactor units.

Olefins can generally be produced at a wide range of temperatures.

An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 500° C. is preferred.

Because of the nature of the process, the process of the present invention may desirably be carried out by use of the molecular sieve catalysts in a dynamic bed system or any system of a variety of transport beds rather than in a fixed bed system. The critical feature of the reactor system utilized is the ability to operate at high space velocities.

The conversion of oxygenates to produce light olefins may be carried out in a variety of catalytic reactors, including, but not limited to, fluid bed reactors and concurrent riser reactors as described in "Free Fall Reactor," *Fluidization Engineering*, D. Kunii and O. Levenspiel, Robert E. Krieger Publishing Co. NY, 1977, incorporated in its entirety herein by reference. Additionally, countercurrent free fall reactors may be used in the conversion process as described in U.S. Pat. No. 4,068,136 and "Riser Reactor", *Fluidization and Fluid-Particle Systems*, pages 48–59, F. A. Zenz and D. F. Othmo, Reinhold Publishing Corp., NY 1960 are also incorporated in their entirety herein by reference. It is well understood by those skilled in the art that each type of reactor will have advantages and disadvantages in any particular application.

Any standard reactor system can be used, including fixed bed or moving bed systems, with a weight hourly space velocity (WHSV) of from 1 hr$^{-1}$ to 1000 hr$^{-1}$, with WHSV being defined as the weight of oxygenate in the feed per hour per weight of the molecular sieve content of the catalyst. Preferred reactors are co-current riser reactors and short contact time countercurrent free-fall reactors in which an oxygenate feedstock can be contacted with a molecular sieve catalyst at a WHSV of at least about 20 hr$^{-1}$, preferably in the range of from about 20 hr$^{-1}$ to 1000 hr$^{-1}$, and most preferably in the range of from about 20 hr$^{-1}$ to 500 hr$^{-1}$. Because the catalyst or the feedstock may contain other materials which act as inerts or diluents, the WHSV is calculated on the weight basis of the oxygenate feed and the molecular sieve used.

It is highly desirable to operate at a temperature of at least 300° C. and a Temperature Corrected Normalized Methane Sensitivity (TCNMS) of less than about 0.016. It is particularly preferred that the reaction conditions for making olefin from oxygenate comprise a WHSV of at least about 20 hr$^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Effective pressures may be in, but are not necessarily limited to, pressures of from about 0.1 kPa to about 100 MPa. Preferred pressures are in the range of about 6.9 kPa to about 34 MPa, with the most preferred range being of from about 48 kPa to about 0.34 MPa. The foregoing pressures are exclusive of any inert diluent, and thus, refer to the partial pressure of the oxygenate compounds and/or mixtures thereof with feedstock. At the lower and upper end of the foregoing pressure ranges, the rate of selectivity, conversion and/or reaction may not be optimum.

The residence time may vary from seconds to a number of hours, determined largely by the reaction temperature, the pressure, the molecular sieve catalyst selected, the WHSV, the phase (liquid or vapor), and the process design characteristics.

One or more inert diluents may be present in the feedstock, for example, in an amount of from 1 to 99 molar percent, based on the total number of moles of all feed and diluent components fed to the reaction zone (or catalyst). Typical diluents include, but are not necessarily limited to, helium, argon, nitrogen, carbon monoxide, carbon dioxide, hydrogen, water, paraffins, alkanes (especially methane, ethane, and propane), alkylenes, aromatic compounds, and mixtures thereof. The preferred diluents are water and nitrogen. Water can be injected in either liquid or vapor form.

The process may be carried out in a batch, semi-continuous or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of the molecular sieves in series to provide for a desired product mixture.

The level of conversion of the oxygenates—particularly during a steady state of the reaction—can be maintained to reduce the level of unwanted by-products. Conversion can also be maintained sufficiently high to avoid the need for commercially unacceptable levels of recycling of unreacted feeds. A reduction in unwanted by-products is seen when conversion moves from 100 mol % to about 98 mol % or less. Recycling up to as much as about 50 mol % of the feed is commercially acceptable. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is required, the catalyst can be continuously introduced as a moving bed to a regeneration zone where it can be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, and the like). The aliphatic moiety preferably contains from 1 to 10 carbon atoms and more preferably contains from 1 to 4 carbon atoms. Representative oxygenates include, but are not necessarily limited to, lower straight and branched chain aliphatic alcohols and their unsaturated counterparts. Examples of suitable compounds include, but are not limited to, the following: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof.

Preferred oxygenate feedstocks are methanol, dimethyl ether and mixtures thereof. The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, and making synthesis gas, then converting the synthesis gas to alcohol or ether. Synthesis gas can be produced by known processes such as steam reforming, autothermal reforming and partial oxidization.

One skilled in the art will appreciate that the olefins produced by the oxygenate-to-olefin conversion reaction of the present invention can be polymerized to from polyolefins. Processes for forming polyolefins from olefins are known in the art. Catalytic processes are preferred. Particularly preferred are metallocene, Ziegler/Natta and acid catalytic systems. Prior to being subjected to a polymerization process, the olefin products are recovered from the products of the oxygenate-to-olefin conversion reaction.

Persons of ordinary skill in the art will recognize that many modifications may be made to the present invention without departing from the spirit and scope of the present invention. The embodiment described herein is meant to be illustrative only and should not be taken as limiting the invention, which is defined by the following claims.

What is claimed is:

1. A method for converting an oxygenate to an olefin, said method comprising the following steps:

providing a source of a silicon-containing composition;

providing a source of an aluminum-containing composition;

providing a source of a phosphorous-containing composition;

providing a template;

forming a reaction mixture sufficient to form a SAPO molecular sieve from said source of a silicon-containing composition, said source of an aluminum-containing composition, said source of phosphorous-containing composition, and said template, said reaction mixture having a first pH;

determining a pH increase in said reaction mixture such that said reaction mixture has a second pH higher than said first pH; and adding, after said determining said pH increase, an acid to said reaction mixture to adjust said second pH to from said first pH plus about one pH unit to said first pH minus about one pH unit;

crystallizing SAPO molecular sieve from the reaction mixture; and contacting an oxygenate with the crystallized SAPO molecular sieve catalyst to convert the oxygenate to olefin.

2. The method of claim 1 further including the step of heating said reaction mixture prior to said step of determining said pH increase.

3. The method of claim 2 further including the step of forming of said crystals after said step of adding an acid to said reaction mixture.

4. The method of claim 3 wherein said acid is added to said reaction mixture at least two times.

5. The method of claim 4 said acid is added to said reaction mixture discontinuously.

6. The method of claim 4 wherein said acid is added to said reaction mixture continuously.

7. The method of claim 1 wherein said template is a dual template.

8. The method of claim 7 wherein said dual template comprises tetraethylammonium hydroxide and dipropylamine.

9. The method of claim 1 wherein said source of a phosphorous-containing composition and said template are both tetraethylammonium phosphate.

10. The method of claim 1 further including the steps of cooling said reaction mixture prior to said adding of said acid to said reaction mixture and heating said reaction mixture after said acid is added to said reaction mixture.

11. The method of claim 3 wherein said acid is selected from the group consisting of phosphoric acid, hydrochloric acid, nitric acid, carbonic acid, sulfuric acid, acetic acid and formic acid.

12. The method of claim 1 wherein said second pH of said reaction mixture is adjusted to from said first pH plus about 0.5 pH unit to said first pH minus about 0.5 pH unit.

13. The method of claim 12 wherein said pH of said reaction mixture is adjusted to a pH from said first pH plus about 0.2 pH unit to said first pH minus about 0.2 pH unit.

14. The method of claim 1 wherein said silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and the metal substituted forms thereof.

15. The method of claim 14 wherein said silicoaluminophosphate molecular sieve is selected from the group consisting of SAPO-5, SAPO-11, SAPO-20, SAPO-31, SAPO-34, and SAPO-42, and the metal substituted forms thereof.

16. The method of claim 1 wherein said SAPO molecular sieve is SAPO-34.

* * * * *